US010460158B2

United States Patent
Perbet et al.

(10) Patent No.: US 10,460,158 B2
(45) Date of Patent: Oct. 29, 2019

(54) METHODS AND SYSTEMS FOR GENERATING A THREE DIMENSIONAL REPRESENTATION OF A HUMAN BODY SHAPE

(71) Applicant: KABUSHIKI KAISHA TOSHIBA, Minato-ku (JP)

(72) Inventors: Frank Perbet, Cambridge (GB); Minh-Tri Pham, Cambridge (GB); Bjorn Stenger, Cambridge (GB); Sam Johnson, Cambridge (GB)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 301 days.

(21) Appl. No.: 15/117,735

(22) PCT Filed: Jun. 19, 2014

(86) PCT No.: PCT/GB2014/051891
§ 371 (c)(1),
(2) Date: Aug. 10, 2016

(87) PCT Pub. No.: WO2015/193628
PCT Pub. Date: Dec. 23, 2015

(65) Prior Publication Data
US 2017/0147874 A1  May 25, 2017

(51) Int. Cl.
*G06K 9/00* (2006.01)
*G06Q 30/06* (2012.01)
(Continued)

(52) U.S. Cl.
CPC ........ *G06K 9/00362* (2013.01); *A61B 5/1077* (2013.01); *A61B 5/1079* (2013.01);
(Continued)

(58) Field of Classification Search
CPC ........... G06T 2207/30196; G06T 7/187; G06T 17/10; G06K 9/00362
See application file for complete search history.

(56) References Cited

U.S. PATENT DOCUMENTS 10,019,838 B2 * 7/2018 Liu .......................... G06T 15/04
10,028,070 B1 * 7/2018 Gamper .................. H04S 7/302
(Continued)

FOREIGN PATENT DOCUMENTS

GB       2504711 A     2/2014
WO  WO 2012/075298 A2  6/2012

OTHER PUBLICATIONS

Perbet, Frank & Stenger, Bjorn & Maki, Atsuto. (2009). Random Forest Clustering and Application to Video Segmentation. British Machine Vision Conference, BMVC 2009—Proceedings. 10.5244/C.23.100.*

(Continued)

*Primary Examiner* — Chan S Park
*Assistant Examiner* — Mai H Tran
(74) *Attorney, Agent, or Firm* — Oblon, McClelland, Maier & Neustadt, L.L.P.

(57) ABSTRACT

In a method of generating a three dimensional representation of a human body shape from a depth image of a clothed human subject is disclosed. The method comprises identifying at least one sample from a plurality of pre-calculated representative samples, each pre-calculated representative sample comprising a three dimensional representation of a human body shape and a corresponding depth map, by comparing the depth maps of the pre-calculated representative samples with the depth image of the clothed human subject; determining a neighbourhood of the data space of possible depth images of unclothed human body shapes from the depth map of the at least one representative sample; generating a parametric model for the human body shape (Continued)

from a neighbourhood of the data space of human body shapes, the neighbourhood of the data space of human body shapes corresponding to the neighbourhood of the data space of possible depth images of unclothed human body shapes; and generating the three dimensional representation of the human body shape by fitting the parametric model to the depth image of the clothed human subject.

18 Claims, 7 Drawing Sheets

(51) Int. Cl.
    *H04N 13/204*      (2018.01)
    *A61B 5/107*      (2006.01)
    *G06K 9/62*      (2006.01)
    *G06T 17/10*      (2006.01)

(52) U.S. Cl.
    CPC ....... *G06K 9/00201* (2013.01); *G06K 9/6202* (2013.01); *G06Q 30/0643* (2013.01); *G06T 17/10* (2013.01); *H04N 13/204* (2018.05); *A61B 5/107* (2013.01)

(56) References Cited

U.S. PATENT DOCUMENTS

| | | | |
|---|---|---|---|
| 10,032,090 B2 * | 7/2018 | Vlutters | A61M 16/06 |
| 10,033,979 B2 * | 7/2018 | Kanaujia | H04N 7/181 |
| 10,043,279 B1 * | 8/2018 | Eshet | G06T 7/11 |
| 2010/0111370 A1 * | 5/2010 | Black | G06K 9/00369 382/111 |
| 2011/0025834 A1 * | 2/2011 | Chen | H04N 7/18 348/77 |
| 2011/0109724 A1 | 5/2011 | Mathe et al. | |
| 2012/0287247 A1 * | 11/2012 | Stenger | H04N 13/271 348/47 |

OTHER PUBLICATIONS

Frank Perbet, et al. "Random Forest Clustering and Application to Video Segmentation", Proceedings of the British Machine Vision Conference, XP055160873, Sep. 7, 2009, 10 pages.

Weiss, A. et al. "Home 3D Body Scans from Noisy Image and Range Data" Dept. of Computer Science, Brown University, Providence, RI, USA, 8 Pages.

"ImageTwin" [TC]²Labs, http://www.imagetwin.com/, 3 Pages.
"3D Body Scanning" [TC]², http://www.tc2.com/index_3dbodyscan. html, 2 Pages.

\* cited by examiner

METHODS AND SYSTEMS FOR GENERATING A THREE DIMENSIONAL REPRESENTATION OF A HUMAN BODY SHAPE

FIELD

Embodiments described herein relate generally to generating three dimensional representations of human body shapes from depth images.

BACKGROUND

Estimating the body shape of a person offers the potential for applications in the domains of clothes fitting, fitness analysis, and digital content creation. A number of commercial full-body capture systems exist that have been deployed in a range of retail outlets. Such systems, using laser or structured light scanning, provide accurate reconstructions, but are costly and require a dedicated capture space.

Consumer level depth sensors offer an inexpensive alternative, but pose a number of challenges: The first is the quality and completeness of the data. A second issue in certain settings is clothing. For an accurate measurement users may be willing to undress in the privacy of their home or a dedicated booth. However, for applications in public areas, or for passive measurement, it may be required to estimate the body shape with the user fully dressed.

BRIEF DESCRIPTION OF THE DRAWINGS

In the following, embodiments are described, by way of example only, with reference to the accompanying drawings in which.

DETAILED DESCRIPTION

In an embodiment a method of generating a three dimensional representation of a human body shape from a depth image of a clothed human subject is disclosed. The method comprises identifying at least one sample from a plurality of pre-calculated representative samples, each pre-calculated representative sample comprising a three dimensional representation of a human body shape and a corresponding depth map, by comparing the depth maps of the pre-calculated representative samples with the depth image of the clothed human subject; determining a neighbourhood of the data space of possible depth images of unclothed human body shapes from the depth map of the at least one representative sample; generating a parametric model for the human body shape from a neighbourhood of the data space of human body shapes, the neighbourhood of the data space of human body shapes corresponding to the neighbourhood of the data space of possible depth images of unclothed human body shapes; and generating the three dimensional representation of the human body shape by fitting the parametric model to the depth image of the clothed human subject.

In an embodiment identifying at least one representative sample from a plurality of pre-calculated representative samples comprises traversing a graph comprising a plurality of trees, each tree comprising a plurality of nodes.

In an embodiment the graph further comprises a plurality of edges between trees.

In an embodiment each tree of the plurality of trees defines a hierarchical splitting of the data space of possible depth images of unclothed human body shapes and the edges between the trees connect nodes corresponding to regions of the data space of possible depth images of unclothed human body shapes which overlap.

In an embodiment comparing the depth maps of the pre-calculated representative samples with the depth image of the clothed comprises evaluating an inside function, wherein the inside function introduces a penalty for points on the depth maps of the pre-calculated representative samples which lie outside and/or in front of points on the depth image.

In an embodiment determining a neighbourhood of the data space of possible depth images of unclothed human body shapes comprises determining a region of the data space of possible depth images of unclothed human body shapes from the depth maps of the representative samples in the set of representative samples; and determining the neighbourhood of the data space of possible depth images of unclothed human body shapes by expanding the region.

In an embodiment the method further comprises identifying a set of representative samples from the plurality of pre-calculated representative samples.

In an embodiment the method further comprises calculating a size indicator and/or a measurement of the subject from the three dimensional representation.

In an embodiment system for generating a three dimensional representation of a human body shape from a depth image of a clothed human subject is disclosed. The system comprises storage for a plurality of pre-calculated representative samples, each pre-calculated representative sample comprising a three dimensional representation of a human body shape and a corresponding depth map; and a processor operable to identify at least one representative sample from the plurality of pre-calculated representative samples by comparing the depth maps of the pre-calculated representative samples with the depth image of the clothed human subject; determine a neighbourhood of the data space of possible depth images of unclothed human body shapes from the depth map of the at least one representative sample; generate a parametric model for the human body shape from a neighbourhood of the data space of human body shapes, the neighbourhood of the data space of human body shapes corresponding to the neighbourhood of the data space of possible depth images of unclothed human body shapes; and generate the three dimensional representation of the human body shape by fitting the parametric model to the depth image of the clothed human subject.

In an embodiment the system further comprises storage for a graph comprising a plurality of trees, each tree comprising a plurality of nodes and wherein the processor is operable to identify the at least one representative sample from the plurality of pre-calculated representative samples by traversing the graph.

In an embodiment the graph further comprises a plurality of edges between trees.

In an embodiment each tree of the plurality of trees defines a hierarchical splitting of the data space of possible depth images of unclothed human body shapes and the edges between the trees connect nodes corresponding to regions of the data space of possible depth images of unclothed human body shapes which overlap.

In an embodiment the processor is operable to compare the depth maps of the pre-calculated representative samples with the depth image of the clothed by evaluating an inside function, wherein the inside function introduces a penalty for points on the depth maps of the pre-calculated representative samples which lie outside and/or in front of points on the depth image.

In an embodiment the processor is operable to determine the neighbourhood of the data space of possible depth images of unclothed human body shapes by determining a region of the data space of possible depth images of unclothed human body shapes from the depth maps of the representative samples in the set of representative samples; and the processor is operable to determine the neighbourhood of the data space of possible depth images of unclothed human body shapes by expanding the region.

In an embodiment the processor is operable to identify a set of representative samples from the plurality of pre-calculated representative samples.

In an embodiment the processor is further operable to calculate a size indicator and/or a measurement of the subject from the three dimensional representation.

In an embodiment the system further comprises a depth sensor operable to capture the depth image of the clothed human subject.

The described embodiments can be incorporated into a specific hardware device, a general purpose device configured by suitable software, or a combination of both. Aspects can be embodied in a software product, either as a complete software implementation, or as an add-on component for modification or enhancement of existing software (such as a plug in). Such a software product could be embodied in a carrier medium, such as a storage medium (e.g. an optical disk or a mass storage memory such as a FLASH memory) or a signal medium (such as a download). Specific hardware devices suitable for the embodiment could include an application specific device such as an ASIC, an FPGA or a DSP, or other dedicated functional hardware means. The reader will understand that none of the foregoing discussion of embodiment in software or hardware limits future implementation of the invention on yet to be discovered or defined means of execution.

Figure 1:
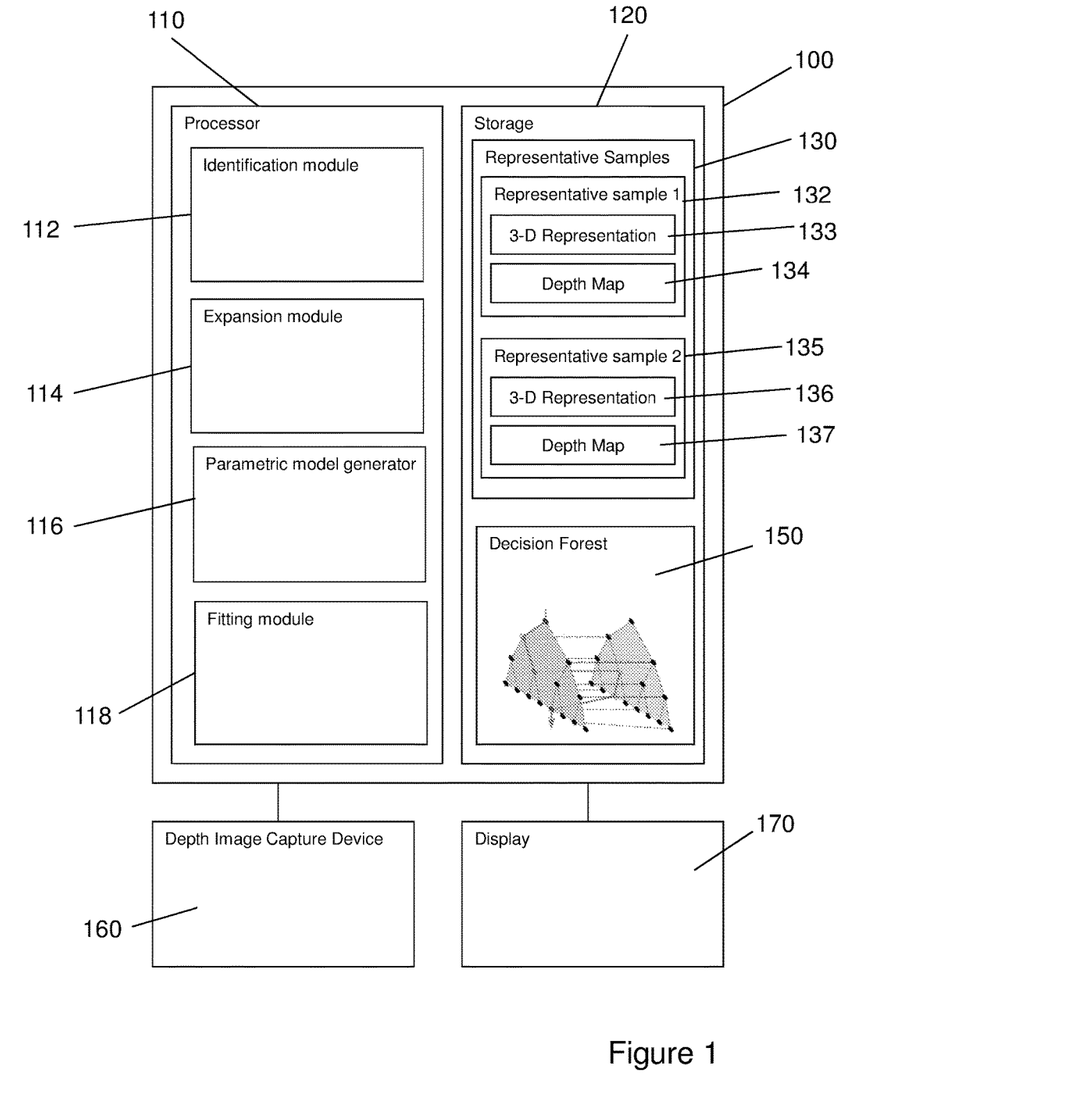
FIG. 1 shows a system for generating a three dimensional representation of a human subject according to an embodiment.

FIG. 1 shows a system for generating a three dimensional representation of a human body shape from a depth image according to an embodiment. The system 100 comprises a processor 110 and storage 120. The processor 110 executes a computer program comprising an identification module 112, an expansion module 114, a parametric model generator 116 and a fitting module 118. The storage 120 stores a plurality of representative samples 130. As shown in FIG. 1, a first representative sample 132 comprises a three dimensional representation of a human subject 133 and a depth map 134 corresponding to the three dimensional representation 133. A second representative sample 135 comprises a three dimensional representation of a human subject 136 and a depth map 137 corresponding to the three dimensional representation 136. The storage 120 stores a decision forest 150.

The system 100 is coupled to a depth image capture device 160 and a display 170. The system may also comprise a camera. The camera may be integrated with the depth image capture device or may be a separate device.

The identification module 112, the expansion module 114, the parametric model generator 116 and the fitting module 118 are computer program modules. They may be implemented as computer software running on a general purpose processor or may be specifically programmed hardware modules or a combination of the two.

Figure 2:
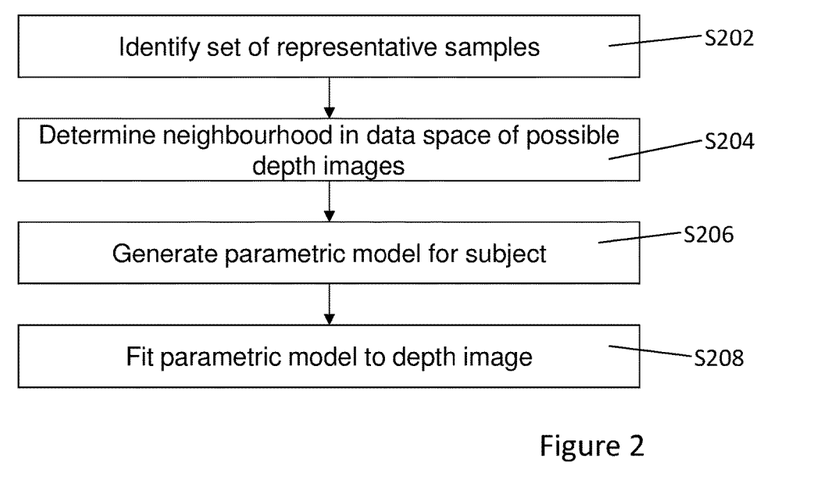
FIG. 2 shows a method of generating a three dimensional representation of a human subject according to an embodiment.

FIG. 2 shows a method of generating a three dimensional representation of a subject from a depth image which is executed by the identification module 112, the expansion module 114, the parametric model generator 116 and the fitting module 118 on the processor 110.

The depth image may be captured by the depth image capture device 160. Alternatively, the method may be carried out on a depth image transferred to the system 100 either over a network or on a storage medium.

The method may be started using a manual trigger such as button or a remote control. Alternatively, the method may be triggered by a voice or gesture command.

The method may be automatically triggered in different ways. If a person is detected standing in a particular area the method may be automatically triggered. This detection may be as a result of a detection from the depth image capture device, or by a detection from a separate sensor located on the floor.

In step S202 a set of representative samples is identified. The set of representative samples is identified from among the pre-calculated representative samples stored in the storage 120. The identification module 112 uses the decision forest 150 to compare the input depth image of a clothed human subject with the depth maps of the representative samples. It is noted that the depth maps of the representative samples correspond to unclothed human body shapes, whereas the input depth image is of a clothed human subject.

In step S204, a neighbourhood of the manifold or data space of possible depth images is determined. This determination is carried out by the expansion module. The set of representative samples occupies a region of the manifold or data space of depth maps of unclothed human subjects. The expansion module determines the neighbourhood of the manifold by expanding this region.

In step S206, a parametric model for the human subject is generated from the neighbourhood of the manifold.

Each representative model also contains pose and shape parameters. The parametric model is built from two sets of principal component analysis (PCA) coefficients, one set of PCA coefficients for the pose, another set of PCA coefficients for the shape.

In step S208, the parametric model is fitted to the depth image to generate the three dimensional representation of the human subject. Typically, around 20 coefficients for the pose and 50 coefficients for the shape are kept, so a function with about 70 input parameters are optimized in step S208.

It is noted that what is determined by steps S202 and S204 is a collection of representative samples that belong to the same neighbourhood. So that principal component analysis can be performed. Therefore, the expansion step could be skipped if a large number of nearest neighbours which all belonged to the same neighbourhood could be computed. Thus, in an embodiment, a large number of representative samples form the set determined in step S202 and the neighbourhood is determined from the set without a separate expansion step.

However, since the cost function is not a proper distance and the method takes place on a manifold, a potential issue here is that all the nearest neighbours might not belong to the same neighbourhood and be quite far apart.

In an alternative embodiment, in step S202, a single representative sample is identified. Then in step S204, the neighbourhood is determined by expanding from this single representative sample.

Segmented, non-clothed human depth images lie on a low-dimensional manifold embedded in the ambient space of all possible depth images. Given an input depth image which contains clothing embodiments described herein localize it on the manifold and use the generating parameters of the local neighbourhood to learn a statistical model for optimization.

Figure 3:
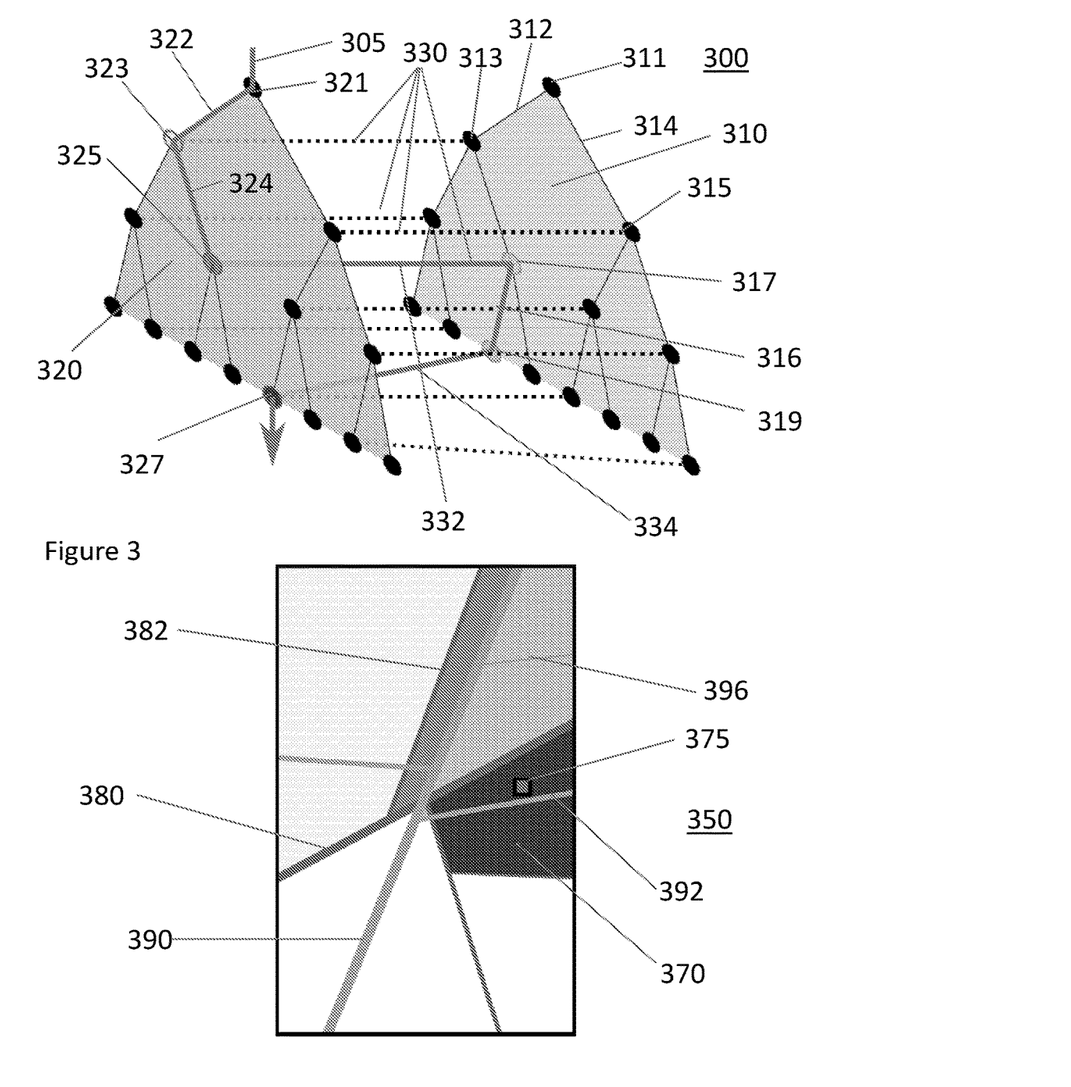
FIG. 3 shows a decision forest and search space used in an embodiment.

FIG. 3 shows a decision forest 300 and a manifold or search space 350 according to an embodiment. The decision forest 300 is a multi-resolution manifold forest and may form the decision forest 150 shown in FIG. 1. The decision forest 300 comprises a plurality of trees. FIG. 3 shows a first tree 310 and a second tree 320. Each of the trees partition the search space 350. The manifold learning data structure of the decision forest 300 is based on randomized decision forests. In addition to the standard vertical moves, additionally allow horizontal traversal between tree nodes is also allowed, based on a learned manifold graph.

The first tree 310 comprises a plurality of nodes 311, 313, 315 and a plurality of links 312, 314 between the nodes. The second tree 320 comprises a plurality of nodes 321, 323, 325, 327 and a plurality of links 322, 324 between the nodes. Additionally, the decision forest 300 comprises a plurality of links 330 between the first tree 310 and the second tree 320. A mean value of a parameter of the search space is associated with each of the nodes of the trees.

A single search path of the decision forest 300 to find a region of the search space 350 with the closest mean to an input requires moving between trees.

FIG. 3 shows a search path 305 in the decision forest 300 and corresponding regions of the search space 350. The example search path 305 starts at a node 321 of the second tree 300. The node 321 of the second tree divides the search space 350 into two regions along a split line 380.

It is noted that at each node of the tree, the test that is performed is a heuristic and does not give a strong guarantee that the closest point on the manifold lies on that branch of the tree. So as the tree is traversed, it is known that the correct part of the manifold is being focussed in on; however, the solution can be in a completely different branch of the tree. Further, in a tree, two nodes which are close geometrically on the manifold might be far away topologically. That is, their shared ancestor might be as high as the tree root. Therefore, the tree traversal is non-optimal because each node test is a heuristic. An example of this can be seen in FIG. 3 as the location on the manifold corresponding to the node 327 actually lies below the boundary 380.

The search path 305 continues along branch 322 to node 323. Node 323 splits the search space 350 along split line 382. Following node 323, the search path 305 continues along branch 324 to node 325. At node 325, the search path 305 follows link 332 between the second tree 320 and the first tree 310 to node 317 of the first tree. The node 327 of the first tree 310 splits the search space along a split line 396. It is noted that at the node 327 of the first tree 310, the search space has already been divided along a slit line 390 and a split line 392 which correspond to nodes 311 and 313 which are closer to the root of the first tree 310.

The search path 305 continues along branch 316 to a node 319 of the first tree 310 and then follows a link 334 between the trees to a node 327 of the first tree. This node 327 corresponds to a region of the search space 370, which includes the point 375 on the search space closest to the input depth image.

The proposed Multi-Resolution Manifold Forest (MRMF) is an ensemble of randomized space partitioning trees which are connected to each other. During training, a graph including the tree edges and edges between trees is learned.

The aim is to learn an ensemble of trees that are balanced while still maintaining randomization between them. Essentially, the trees can be viewed as defining an adaptive grid on the ambient space similar to k-d trees.

The MRMF is a set, T, of binary trees $t_i \varepsilon T$ which hierarchically partition the ambient data space $\mathbb{R}^D$. Each tree is trained with the same dataset (i.e. bagging is not used):

$$\chi = \{X_i\}, X_i \in \mathbb{R}^D$$

It is assumed that the samples $X_i$ to lie on a d-dimensional manifold M embedded In $\mathbb{R}^D$ with d<D.

The parameters $\Theta_j = (\theta_j, \tau_j)$ for each node j define a separating hyper plane in the ambient space $\mathbb{R}^D$ by its unit normal $\theta_j \in \mathbb{R}^D$ and a threshold $\tau_j \in \mathbb{R}$.

The data assigned to each node, $X_j$, is partitioned into two subsets: $X^L_j$ and $X^R_j$, depending on the value of the split function:

$$h(X, \Theta_j) \in \{0,1\}$$

The split functions take the form:

$$h(X, \Theta_j) = I(X^T \theta_j > \tau_j)$$

Where $I(\bullet)$ is the indicator function.

The set $X^L_j$ contains samples $X \in \chi$ for which $h(X, \Theta_j) = 0$
The set $X^R_j$ contains samples $X \in \chi$ for which $h(X, \Theta_j) = 1$ To find $\Theta_j$, we sample a random subset, $\mathcal{D}_j \subset \chi_j$, sample a point $\chi_k \in D_j$ and find the most distant point to it in Dj:

$$x_l = \underset{x \in \mathcal{D}_j}{\mathrm{argmax}} \|x_k - x\|.$$

The normal $\Theta_j$, to the hyper plane is the unit vector between these two points:

$$\Theta_j = (X_l - X_k)/(\|X_l - X_k\|)$$

Figure 4:
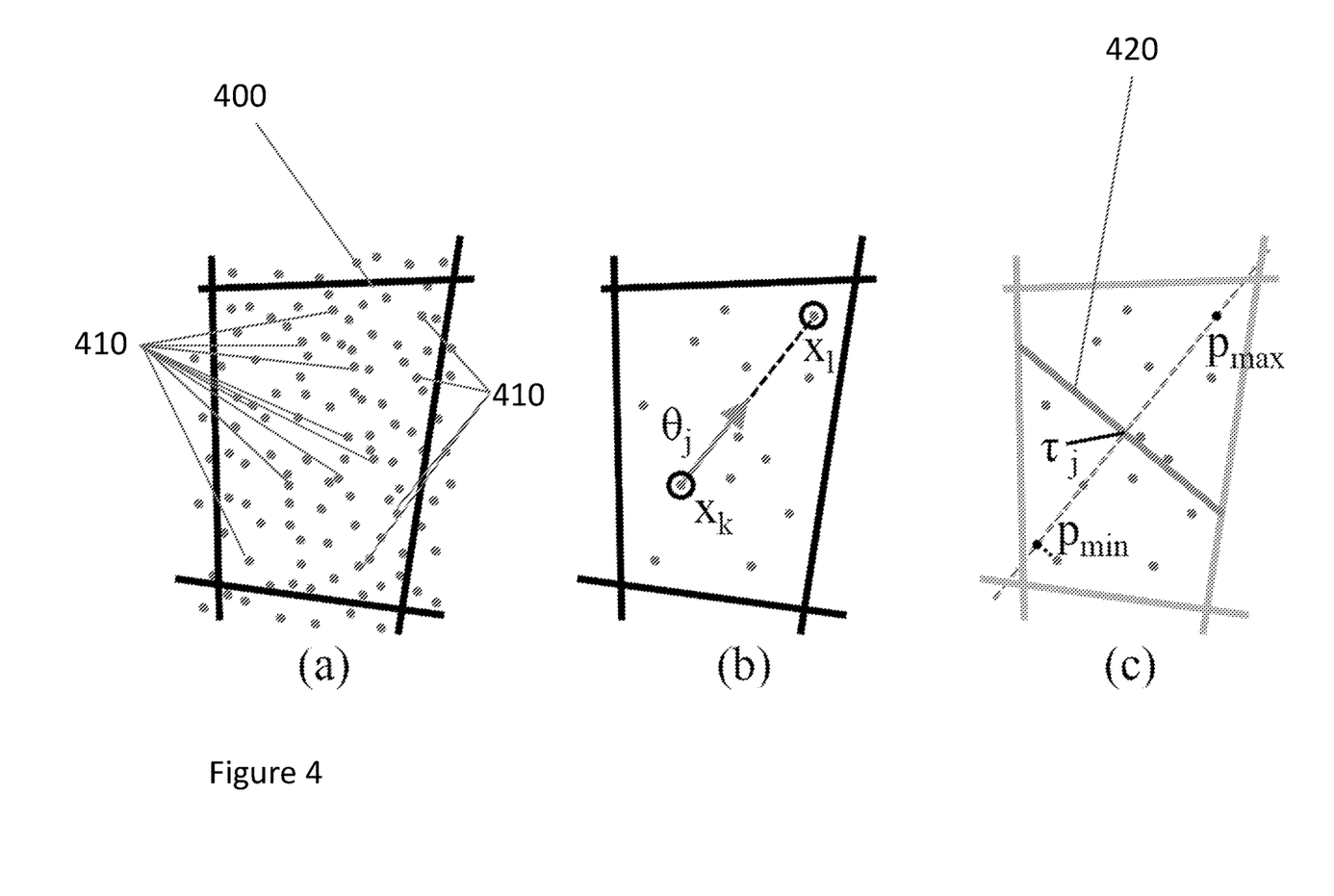
FIG. 4 shows splitting a region of a search space in the generation of a decision forest in an embodiment.

FIG. 4 illustrates the process of splitting a region 400. The region 400 corresponds to a tree node. Split function parameters are selected based on a random subset of points 410 (shown in red in FIG. 4a). A random point $x_k$ and its most distant point $x_l$ within the subset define $\Theta_j$, the normal to a separating hyper plane 420. The hyper plane 420 splits the region halfway between the minimum projected value $p_{min}$ and the maximum projected value $p_{max}$.

As described above, the trees are learned in an unsupervised manner without optimising for a classification or regression objective. Instead, the goal of MRMF is to define a space partitioning adapted to data located on an unknown manifold. To keep the tree approximately balanced, the threshold $\tau_j$ is set to $(p_{max} - p_{min})/2$ where $p_{max}$ and $p_{min}$ are respectively the maximum and minimum values of $p_i = X_i^T \theta_j$ for all $X \in \mathcal{D}_j$.

The set of nodes, V, of the MRMF graph are the nodes of the trees, defined as $v_i^t \in V$ with t the tree and i the node index. The set of edges ε which are all directed is composed of all parent-child edges $\varepsilon_t$ as well as edges between trees $\varepsilon_{s,t}$. Formally, the set of edges is defined as:

$$\varepsilon = \left(\bigcup_{t \in \mathcal{T}} \varepsilon_t\right) \cup \left(\bigcup_{(s,t) \in \mathcal{T}} \varepsilon_{s,t}\right)$$

While $\varepsilon_t$ is defined as part of the tree learning process, learning the inter-tree edges $\varepsilon_{s,t}$ is more involved.

Figure 5:
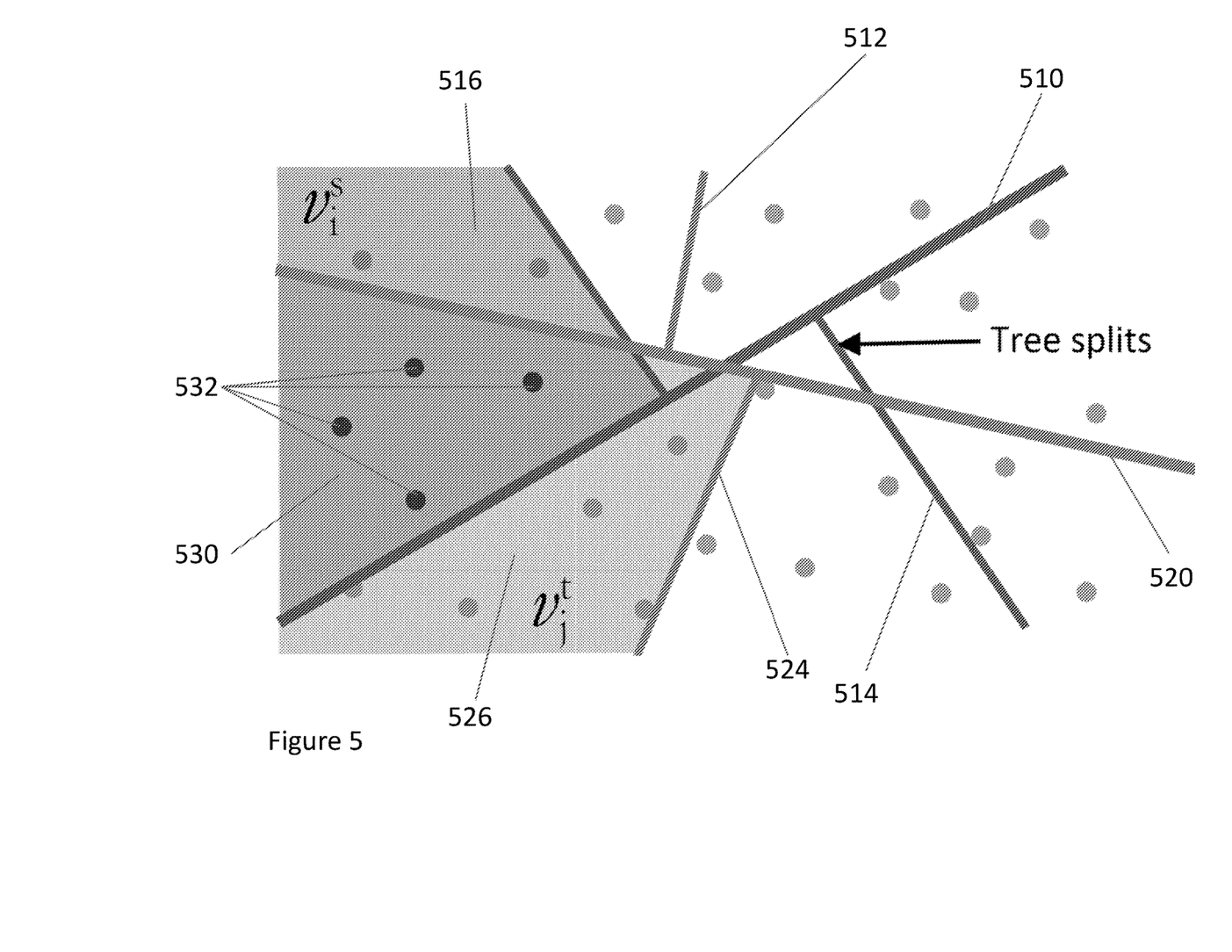
FIG. 5 shows the regions of a search space and the process of learning inter-tree edges in a decision forest of an embodiment.

FIG. 5 shows the process of learning the inter-tree edges. A first tree partitions a region of the data space as shown by the red partitions 510, 512, 514. A second tree partitions the region of the data space as shown by the blue edges 520, 522, 524. A node $v_i^s$ of the first tree thus corresponds to a region 516 of the data space. A node $v_j^t$ of the second tree corresponds to a region 526 of the data space. The MRMF connects nodes whose regions intersect, such as the nodes $v_i^s$ and $v_j^t$. The intersection 530 is detected by data samples belonging to both regions 532. Exact computation of these intersections is expensive in high dimensions, even in the case of linear splits. Instead, the data samples 532 are used estimate intersections, and nodes are connected if intersection of their sample sets is non-empty.

Not all pairs of regions are connected: two regions are connected only if they are tree leaves at the same stage during the training process (trees are grown breadth-first). Doing so ensures that connected regions are of similar volume, resulting in a coarse-to-fine structure. It is noted that exact computation of region volume is expensive in high dimensions, and many regions are open with infinite volume.

In an embodiment, for compactness the implementation of the MRMF graph is pointer-free. The graph is stored in an array, requiring setting a maximum number of edges per node.

The traversal of a MRMF will now be described. The aim is to optimize a function f defined on points that lie on a manifold M. First, an initial solution is located by traversing, both horizontally and vertically, the trained MRMF. Upon reaching a leaf node it is possible to efficiently navigate the local neighbourhood with the horizontal connections and build a local chart.

In order to minimize a function f with an MRMF, first, good initial solutions need to be found. These solutions are points on the manifold M which are hoped to be close to the global solution. It is noted that we are not restricted to finding a single initial solution. Rather we are looking for k candidates from which horizontal searches are initiated.

A course to graph fine walk over the MRMF is then carried out. During tree construction, we keep track of the arithmetic mean $\overline{X}_j^t$ of all the samples in node $v_j^t$. During testing we evaluate the function at those points and choose further nodes to explore by evaluating neighbours on the MRMF graph. Since the $\overline{X}_j^t$ are arithmetic means, they can lie outside the manifold: the only assumption we make on the function f is that it can be evaluated everywhere in the ambient space, that is, for every $X \in \mathbb{R}^D$.

The search strategy is as follows: a priority queue is initialized with all tree roots giving higher priority to nodes with lower cost function values. The current best candidate is removed from the queue and its children added; if they are leaves they are stored as potential results. The method iterates until reaching its budget of function evaluations. Using horizontal moves increases the chance of finding the leaf node in the graph which minimizes f, allowing correction for choices made during early tree traversal.

The output of this approximate discrete function minimization method is given as a list of leaf averages $\overline{x}_j^t$ serving as seed points to compute a local chart on the manifold M. Generally, this can be seen as another characteristic of present method: no graph is explicitly built over the individual training data samples. It is considered that this is an advantage of embodiments as the graph representation is smaller and no information is lost.

All the leaf averages $\overline{x}_j^t$ act as the seeds from which the local chart of the manifold M is computed. Each seed is the starting node of a random walk of horizontal moves in its neighbourhood. The walk continues until a given number of nodes has been reached. This parameter controls the local chart size and must therefore be chosen carefully, depending on a given optimization problem.

A local chart of the manifold M is then computed using Principal Component Analysis (PCA) over the set of nodes reached by the walks (c.f. in differential geometry the tangent space is used to compute a local chart). The mapping is linear and is given by the transformation from the PCA space to the ambient space c(y)=x where y is the vector of coefficients for the first principal components. The chart provides a locally linear parameterization of the space, in which standard methods like gradient descent can be used to minimize the function f° C. w.r.t. y. To account for local curvature, using the chart is restricted within a given range of the PCA components. Outside this range, a new chart is recomputed around the new initial solution.

The estimation of human bodies obscured by clothing is formulated as optimization over the manifold of unclothed body shapes. The function to be optimized is asymmetric—we wish to find a solution on the manifold, i.e. a nude body shape, which lies inside the clothed input. The MRMF allows efficient optimization of such asymmetric functions.

The model is learned from synthetic depth measurement images (vectorized as x) which are smoothed and sub-sampled.

Figure 6:
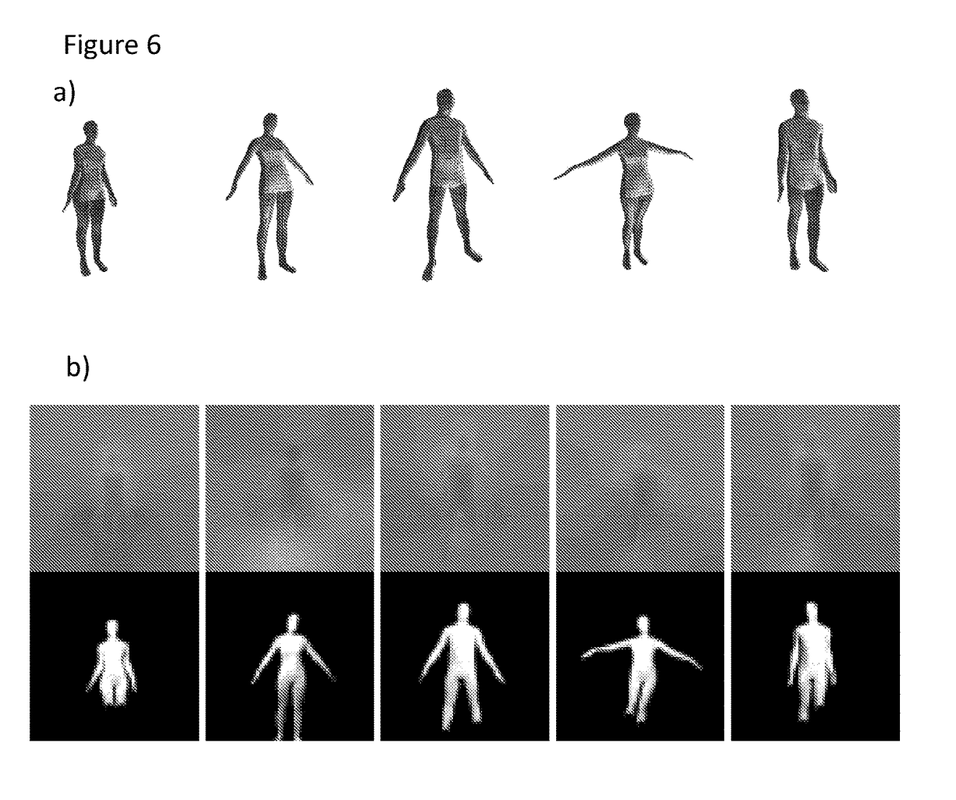
FIG. 6 shows training data used for body shape estimation in an embodiment.

FIG. 6 shows the training data used for body shape estimation. FIG. 6a shows training meshes and FIG. 6b shows sub-sampled measurement images which are simulated from the training meshes. The manifold of segmented human depth measurements is learned from the synthetically rendered samples shown in FIG. 6a. The first row shows synthetic 3D meshes generated during training, the second row shows the smoothed and sub-sampled virtual depth measurement and silhouette images from which a manifold is learned. The samples shown here are representative of the pose variation which is used for training.

Every element $x \in X$ is defined as $\ddot{x} = (x^\alpha, x^d)$

With $X^\alpha$ representing the amount of valid information at each pixel, computed from the blurred and sub-sampled silhouette image, and $X^d$ the depth value, computed from the silhouette and depth images using the pre-multiplied alpha compositing method. The dissimilarity measure is defined between input x and points on the manifold y as $$d(x, y) = \sum_{i=1}^{|x|} k(v(x_i^\alpha, y_i^\alpha)) + k(v(x_i^\alpha x_i^d, y_i^\alpha y_i^d))$$

With the inside function v(x, y) being defined as $$v(x,y)=|(x-y)(1+I(x<y)\beta)|$$

and where k( ) is a kernel function reducing the influence of outliers. This function induces a penalty of β for manifold points that are greater than input points in either α or depth, i.e. they either lie outside the input or in front of it. Here it is noted that a property of the camera model used is that depth values are negated.

Initial solutions on the manifold are computed using the approach described above. We then perform a random walk to find a neighbourhood within which to build a parametric body model.

For the final estimation of body shape we revert to a standard ICP approach between the original high-resolution point cloud and our parametric body model. The parametric body model is built from the vector field of generating parameters attached to the manifold neighbourhood found previously. Our ICP optimization minimizes the following energy function:

$$E(\Phi)=E_d(\Phi,q)+\gamma E_r(\Phi)$$

Where $$\Phi=(\Phi_s,\Phi_p)$$

Are the parameters for the shape and pose respectively, and q are the corresponding points in the input depth map to each vertex of our model. The data term $E_d$ is defined as $$E_d(\Phi, q) = \sum_{i=1}^{|q|} k(d(m(\Phi)_i, q_i)/\sigma)$$

Where $m(\Phi)_i$ generates the model vertex in correspondence with $q_i$, $d(\cdot)$ is a distance function defined below, σ is the noise level, and k a kernel function which increases robustness to outliers. The distance we use is a modified point-to-plane distance of the form:

$$d(p,q)=\text{inside}((p-q)^T n_q)$$

where $n_q$ is the normal at point q. The clothing-robust inside term, $$\text{inside}(y)=y(1-I(y<0)\pi_{inside})$$

gives preference to models beyond the measured depth, i.e. the naked shape is within the clothed shape.

We iterate between minimizing the equation above for E(Φ) with Levenberg-Marquardt and finding correspondences. In the correspondence stage we restrict point-to-model matches based on normal directions to improve accuracy.

Embodiments described are able to optimize asymmetric similarity measures between input points and the learned manifold and handle noisy observations.

The accuracy of an embodiment is discussed below. Given a noisy, incomplete depth sensor input of a clothed person we estimate their body shape by learning a manifold of depth maps rendered from unclothed human body shapes. Given a clothed input image we use an asymmetric similarity function robust to clothing to optimize on the manifold. We evaluate the accuracy from four physical measurements taken from eight subjects—height, waist circumference, chest circumference, and shoulder width. From the eight subjects we capture ten depth measurements with varying pose. We define paths for the same physical measurements on the mesh model. This allows us to predict the measurements from an estimation result. All model parameters were estimated on a separate validation dataset of different people.

To collect training data we registered a 3D model to 4,281 scans a dataset, obtaining a set of registered human meshes with corresponding pose skeletons. We perform an inversion of Linear Blend Skinning (LBS) to 'unskin' each registered mesh into the mean pose. From this set of normalized meshes we generate ten million virtual samples via interpolation (applied to shapes belonging to the same gender). These are perturbed locally by sampling from a learned pose model. To generate virtual depth images we render each model using a virtual camera setup matching the physical setup. During both capture and rendering the depth images are normalized such that the first two directions of maximum variance in 3D space lie parallel to the imaging plane. The normalized depth images are smoothed and down-sampled to 64×64. The MRMF consists of ten trees of depth 18.

We evaluate the use of the inside term over simple Euclidean distance between the input depth map and the manifold. It was found that the error of the initialization decreases from 10.16 cm to 5.31 cm, demonstrating the benefit of the inside term.

To evaluate the robustness of the cost function to different clothing, the shape estimation accuracy was measured over eight clothing types worn by the same person.

Figure 7:
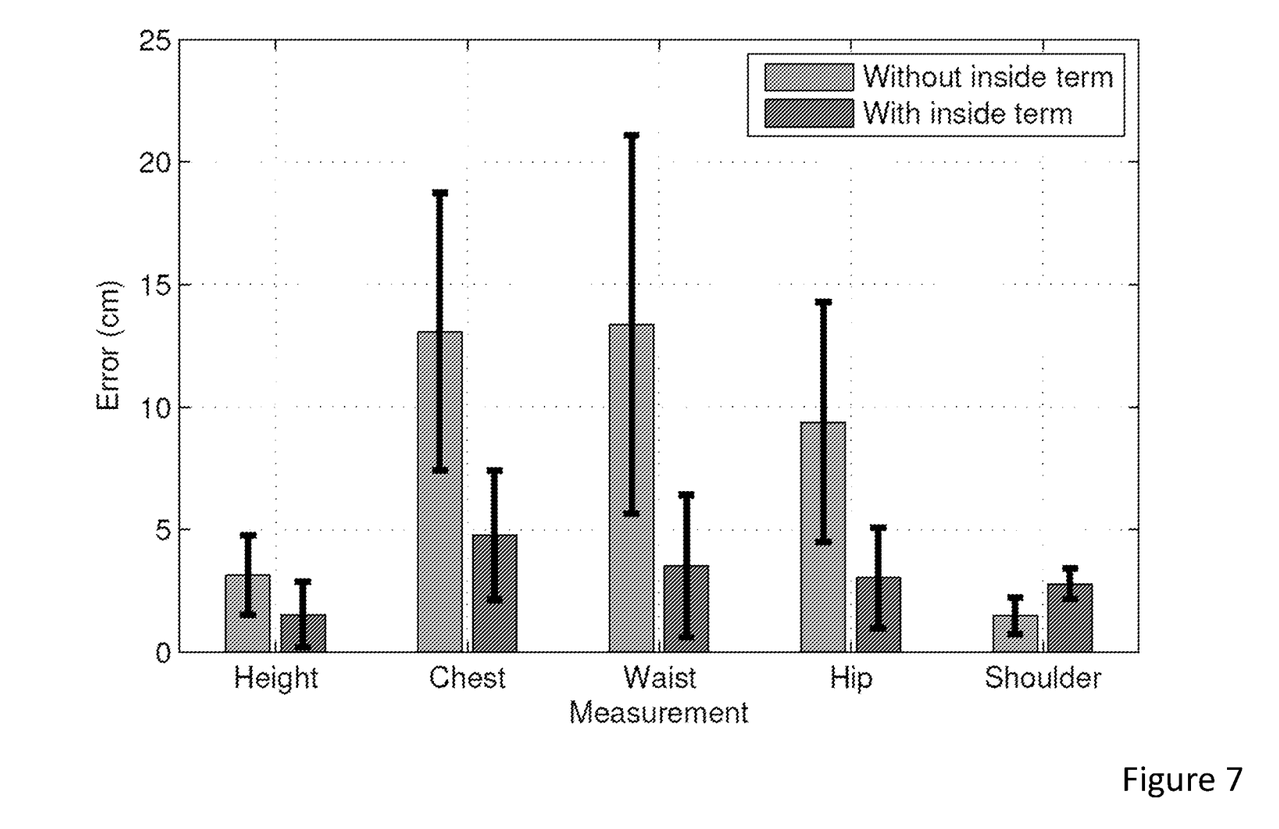
FIG. 7 shows the effect of the use of an inside term on error in an embodiment.

FIG. 7 shows the effect of the inside term for five physical measurements over eight different clothing types on a single person. The mean error and variance of the error are plotted. As can be seen from FIG. 7, the use of the inside term dramatically reduces the both the size and the variance of the error.

In an embodiment the methods and systems described above are used in health and body shape monitoring. The impact on a subject of diet or exercise is visualised and assessed. Future body shape may be predicted and assessed. Embodiments allow the visualisation and tracking of a full body shape. This is easier to visualise and may be more motivational than single measures such as waist measurements or weight measurements.

Embodiments have applications in clothing retail. For example, embodiments allow consumers a highly accurate way to visualise clothing. Further, precise and accurate measurements can be taken for made to measure clothing even in an online environment.

Embodiments may be applied to online gaming and communication. Realistic avatars can be created which closely match a subject's body shape. Compression of video including people may be improved since body shape and texture parameters only need to be sent once and the pose could be updated for subsequent times.

Embodiments have applications in tracking people in video sequences. Once a body shape is known, the person having the shape can be tracked in frames of a video sequence and may be re-identified even in sequences captured by a different camera.

Embodiments have applications in biometrics. For example Body shape estimation allows passive access control in office buildings. Body shape combined with other passive biometrics such as gait and posture allow improved identity verification. The ability to estimate body weight passively may be useful flight tickets priced by body weight.

Embodiments have applications in security. Body shape estimation can be used to detect hidden items under clothing. The estimation of body shape and comparison between customers entering and leaving a store can provide shoplifting detection. The estimation and comparison between people at different points in time can detect discrete package drops which is useful in a public security context.

While certain embodiments have been described, these embodiments have been presented by way of example only, and are not intended to limit the scope of the inventions. Indeed, the novel methods, and systems described herein may be embodied in a variety of other forms; furthermore, various omissions, substitutions and changes may be made without departing from the spirit of the inventions. The accompanying claims and their equivalents are intended to cover such forms or modifications as would fall within the scope and spirit of the inventions.

The invention claimed is:

1. A method of generating a three dimensional representation of a human body shape from a depth image of a clothed human subject, the method comprising:
    identifying at least one representative sample from a plurality of pre-calculated representative samples, each pre-calculated representative sample comprising a three dimensional representation of a human body shape and a corresponding depth map, by comparing depth maps of the pre-calculated representative samples with the depth image of the clothed human subject, the depth maps corresponding to unclothed human body shapes;
    determining a neighbourhood of first data space of possible depth images of unclothed human body shapes from the depth map of the at least one representative sample;
    generating a parametric model for the human body shape from a neighbourhood of second data space of human body shapes, the neighbourhood of the second data space of human body shapes corresponding to the neighbourhood of the first data space of possible depth images of the unclothed human body shapes; and
    generating the three dimensional representation of the human body shape by fitting the parametric model to the depth image of the clothed human subject.

2. A method according to claim 1, wherein identifying at least one representative sample from a plurality of pre-calculated representative samples comprises traversing a graph comprising a plurality of trees, each tree comprising a plurality of nodes.

3. A method according to claim 2, wherein the graph further comprises a plurality of edges between trees.

4. A method according to claim 3, wherein each tree of the plurality of trees defines a hierarchical splitting of the first data space of possible depth images of unclothed human body shapes and the edges between the trees connect nodes corresponding to regions of the first data space of possible depth images of unclothed human body shapes which overlap.

5. A method according to claim 1, wherein comparing the depth maps of the pre-calculated representative samples with the depth image of the clothed human subject comprises evaluating an inside function, wherein the inside function introduces a penalty for points on the depth maps of the pre-calculated representative samples which lie outside and/or in front of points on the depth image.

6. A method according to claim 1 wherein determining the neighbourhood of the first data space of possible depth images of unclothed human body shapes comprises:
    determining a region of the first data space of possible depth images of unclothed human body shapes from depth maps of representative samples in a set of the pre-calculated representative samples; and
    determining the neighbourhood of the first data space of possible depth images of unclothed human body shapes by expanding the region.

7. A method according to claim 1, further comprising identifying a set of representative samples from the plurality of pre-calculated representative samples.

8. A method according to claim 1, further comprising calculating a size indicator and/or a measurement of the clothed human subject from the three dimensional representation.

9. A computer readable medium carrying processor executable instructions which when executed on a processor cause the processor to carry out a method according to claim 1.

10. A system for generating a three dimensional representation of a human body shape from a depth image of a clothed human subject, the system comprising:
    storage for a plurality of pre-calculated representative samples, each pre-calculated representative sample comprising a three dimensional representation of a human body shape and a corresponding depth map; and
    a processor operable to:
        identify at least one representative sample from the plurality of pre-calculated representative samples by comparing depth maps of the pre-calculated representative samples with the depth image of the clothed human subject, the depth maps corresponding to unclothed human body shapes;
        determine a neighbourhood of first data space of possible depth images of unclothed human body shapes from the depth map of the at least one representative sample;
        generate a parametric model for the human body shape from a neighbourhood of second data space of human body shapes, the neighbourhood of the second data space of human body shapes corresponding to the neighbourhood of the first data space of possible depth images of the unclothed human body shapes; and
        generate the three dimensional representation of the human body shape by fitting the parametric model to the depth image of the clothed human subject.

11. A system according to claim 10, further comprising storage for a graph comprising a plurality of trees, each tree comprising a plurality of nodes and wherein the processor is operable to identify the at least one representative sample from the plurality of pre-calculated representative samples by traversing the graph.

12. A system according to claim 11, wherein the graph further comprises a plurality of edges between trees.

13. A system according to claim 12, wherein each tree of the plurality of trees defines a hierarchical splitting of the first data space of possible depth images of unclothed human body shapes and the edges between the trees connect nodes corresponding to regions of the first data space of possible depth images of unclothed human body shapes which overlap.

14. A system according to claim 10, wherein the processor is operable to compare the depth maps of the pre-calculated representative samples with the depth image of the clothed human subject by evaluating an inside function, wherein the inside function introduces a penalty for points on the depth maps of the pre-calculated representative samples which lie outside and/or in front of points on the depth image.

15. A system according to claim 10, wherein the processor is operable to determine the neighbourhood of the first data space of possible depth images of unclothed human body shapes by determining a region of the first data space of possible depth images of unclothed human body shapes from depth maps of representative samples in a set of the pre-calculated representative samples; and the processor is operable to determine the neighbourhood of the first data space of possible depth images of unclothed human body shapes by expanding the region.

16. A system according to claim 10, wherein the processor is further operable to identify a set of representative samples from the plurality of pre-calculated representative samples.

17. A system according to claim 10, wherein the processor is further operable to calculate a size indicator and/or a measurement of the clothed human subject from the three dimensional representation.

18. A system according to claim 10, further comprising a depth sensor operable to capture the depth image of the clothed human subject.

* * * * *